(12) United States Patent
Hiraoka

(10) Patent No.: US 9,111,739 B2
(45) Date of Patent: Aug. 18, 2015

(54) IONIZATION METHOD AND APPARATUS USING ELECTROSPRAY, AND ANALYZING METHOD AND APPARATUS

(75) Inventor: Kenzo Hiraoka, Kofu (JP)

(73) Assignee: UNIVERSITY OF YAMANASHI, Yamanashi (JP)

( * ) Notice: Subject to any disclaimer, the term of this patent is extended or adjusted under 35 U.S.C. 154(b) by 0 days.

(21) Appl. No.: 13/491,331

(22) Filed: Jun. 7, 2012

(65) Prior Publication Data

US 2012/0248303 A1    Oct. 4, 2012

Related U.S. Application Data

(63) Continuation-in-part of application No. PCT/JP2010/072511, filed on Dec. 8, 2010.

(30) Foreign Application Priority Data

Dec. 8, 2009    (JP) .................................. 2009-278458

(51) Int. Cl.
  *H01J 49/26*   (2006.01)
  *H01J 49/16*   (2006.01)
  *G01N 30/72*   (2006.01)
  *G01N 1/38*    (2006.01)

(52) U.S. Cl.
  CPC .......... *H01J 49/165* (2013.01); *G01N 30/7266* (2013.01); *H01J 49/167* (2013.01); *G01N 1/38* (2013.01)

(58) Field of Classification Search
  CPC ....... G01N 1/38; G01N 3/7266; H01J 49/165; H01J 49/167

USPC .............................. 250/282, 288, 423 R, 424
See application file for complete search history.

(56) References Cited

U.S. PATENT DOCUMENTS 5,393,975 A * 2/1995 Hail et al. ...................... 250/288
5,945,678 A * 8/1999 Yanagisawa ................ 250/423 F (Continued)

FOREIGN PATENT DOCUMENTS

JP    9-304344 A    11/1997
JP    9-510879 A    11/1997

(Continued)

OTHER PUBLICATIONS

Form PCT/ISA/210 for PCT/JP2010/072511 dated Feb. 22, 2011.

(Continued)

*Primary Examiner* — Jack Berman
*Assistant Examiner* — Wyatt Stoffa
(74) *Attorney, Agent, or Firm* — Birch, Stewart, Kolasch & Birch, LLP

(57) ABSTRACT

It is arranged so that living tissue that has not been pretreated can be adopted as a sample of interest. A sample is introduced into at least a tip portion of a hollow insulated sample holder 11 having a small hole 11a in the tip portion. A slender metal wire 12, which has been inserted into the sample holder 11 from the rear, is projected outwardly from the sample holder 11 through the hole 11a while being brought into contact with the sample. A high voltage is applied to the slender metal wire 12 at least in a portion of a time period in which the tip of the slender metal wire 12 is being projected outwardly from the hole 11a, thereby ionizing, by electrospray, the sample adhering to the tip of the slender metal wire 12. The ions are introduced into an analyzing apparatus and are analyzed.

18 Claims, 9 Drawing Sheets

(56) References Cited

U.S. PATENT DOCUMENTS

| | | | |
|---|---|---|---|
| 6,337,480 B1* | 1/2002 | Andrien et al. | 250/288 |
| 6,573,494 B1* | 6/2003 | Andrien et al. | 250/288 |
| 7,364,913 B2* | 4/2008 | Andrien et al. | 436/173 |
| 7,465,920 B2* | 12/2008 | Hiraoka | 250/288 |
| 2002/0168778 A1* | 11/2002 | Andrien et al. | 436/173 |
| 2003/0160166 A1* | 8/2003 | Glish et al. | 250/288 |
| 2003/0183757 A1 | 10/2003 | Kato | |
| 2003/0202920 A1* | 10/2003 | Kaufman et al. | 422/186 |
| 2004/0072337 A1* | 4/2004 | Moon et al. | 435/287.2 |
| 2006/0118714 A1* | 6/2006 | Sobek et al. | 250/288 |
| 2007/0102634 A1* | 5/2007 | Frey et al. | 250/288 |
| 2007/0202258 A1* | 8/2007 | Yamagata et al. | 427/282 |
| 2007/0221861 A1* | 9/2007 | Lenke et al. | 250/425 |
| 2008/0054176 A1* | 3/2008 | Hiraoka | 250/288 |
| 2008/0054177 A9* | 3/2008 | Andrien et al. | 250/288 |
| 2009/0071815 A1* | 3/2009 | Takamizawa et al. | 204/157.15 |
| 2009/0309020 A1* | 12/2009 | Cooks et al. | 250/282 |
| 2011/0108726 A1* | 5/2011 | Hiraoka et al. | 250/282 |
| 2013/0040402 A1* | 2/2013 | Yang et al. | 436/181 |
| 2014/0315237 A1* | 10/2014 | Masujima et al. | 435/29 |

FOREIGN PATENT DOCUMENTS

| | | |
|---|---|---|
| JP | 10-112279 A | 4/1998 |
| JP | 2006-134877 A | 5/2006 |
| WO | WO 95/10223 A2 | 4/1995 |
| WO | WO 03/065405 A1 | 8/2003 |
| WO | WO 2005/104181 A1 | 11/2005 |
| WO | WO 2007/002405 A2 | 1/2007 |

OTHER PUBLICATIONS

Mizuno, et al., "Live Single-Cell Video-Mass Spectrometry for Cellular and Subcellular Molecular Detection and Cell Classification", Journal of Mass Spectrometry, 2008, vol. 43, pp. 1692-1700.

* cited by examiner

IONIZATION METHOD AND APPARATUS USING ELECTROSPRAY, AND ANALYZING METHOD AND APPARATUS

This application is a Continuation-in-Part of PCT International Application No. PCT/JP2010/072511 filed on Dec. 8, 2010, which claims priority under 35 U.S.C. §119(a) to Application No. 2009-278458 filed in Japan on Dec. 8, 2009, all of which are hereby expressly incorporated by reference into the present application.

BACKGROUND OF THE INVENTION

1. Field of the Invention

The present invention relates to an ionization method and apparatus using electrospray, and to an analyzing method and apparatus.

2. Description of the Related Art

A typical method of imaging mass spectrometry for dealing with biological samples and industrial products and the like is mass spectrometry using matrix-assisted laser desorption ionization (MALDI). With this method, a pretreatment, namely the preparation of a MALDI sample, is required.

The molecular analysis of live single cells has been gaining momentum in recent years, and nano-electrospray (ESI) mass spectrometry has been proposed as an effective analytical method for this purpose.

See Mizuno, Tsuyama, Harada and Masujima "Live single-cell video-mass spectrometry for cellular and subcellular molecular detection and cell classification", J. Mass Spectrom. 2008; 43: 1692-1700.

According to this method, a cell of interest or cellular solution thereof is drawn into the end of a glass ESI tip (a capillary), the end having an opening diameter (inner diameter) on the micron order, an ionization solvent (for example, acetonitrile containing 0.5% formic acid for the positive-ion mode, or 0.5% ammonia water for the negative-ion mode) is applied to the interior of the ESI tip to achieve dilution by $10^6$ times or more, then the diluted cellular sample is ionized by electrospray and the result introduced to an analyzing apparatus. With this method, the solvent also undergoes mass spectrometry as a matter of course, and an ion signal ascribable to molecules resulting from the solvent shows up in the mass spectrometry spectra.

SUMMARY OF THE INVENTION

The present invention provides an ionization method and apparatus that enable living cells or the like, which have not been pretreated, to be adopted as a sample of interest (inclusive of a single cell, the body fluid of a living animal, etc.).

The present invention further provides an ionization method and apparatus that make it possible to desorb and ionize sample ions under atmospheric pressure.

The present invention further provides a method and apparatus capable of producing the electrospray phenomenon even with regard to liquid biological samples and samples having a high salt concentration.

The present invention further provides an ionization method and apparatus using electrospray in which dilution with a solvent is not always necessary.

The present invention further provides an analyzing method and analyzing apparatus for analyzing ions that have been ionized by the above-mentioned ionization method or apparatus.

An ionization method according to the present invention comprises introducing a sample into at least a tip portion of a hollow insulated sample holder having a small hole in the tip portion; supporting an electrically conductive linear body (inclusive of one that is needle-shaped), which has been inserted inside the sample holder, such that a tip thereof is projectable outwardly from or retractable into the hole; projecting the tip of the linear body outwardly from the sample holder through the hole while being brought into contact with the sample inside the sample holder; and applying a high voltage to the linear body at least in a portion of a time period in which the tip of the linear body is being projected outwardly from the hole, thereby ionizing, by electrospray, the sample adhering to the tip of the linear body.

By using the sample holder, a sample can be taken directly at the tip portion thereof. A sample taken separately can also be introduced into the tip portion of the sample holder as a matter of course. An arrangement in which a liquid sample is supplied to the sample holder from liquid chromatography can also be adopted.

If necessary, a solvent may be supplied to a sample inside the sample holder or to a sample adhering to the tip of the electrically conductive linear body.

The application of a high voltage to the linear body at least in a portion of a time period in which the tip of the linear body is being projected outwardly from the hole includes the following modes of implementation: Specifically, a high voltage for electrospray may be applied to the electrically conductive linear body constantly, or a pulsed high voltage may be applied to the electrically conductive linear body after the tip of the electrically conductive linear body is projected outwardly from the hole of the sample holder. In the case of the latter, it is preferred that application of the pulsed high voltage be halted when the sample at the tip of the electrically conductive linear body has been consumed by electrospray. It is preferred that the high voltage be applied across the electrically conductive linear body and an ion introduction passage of an analyzing apparatus.

The small hole provided at the tip portion of the sample holder means a small hole which, at its largest, will not allow a liquid sample, which has been introduced to the tip portion of the sample holder, to leak to the exterior thanks to surface tension, or signifies a hole smaller than this.

In accordance with the present invention, the sample inside the sample holder adheres to the tip of the electrically conductive linear body when the tip of the electrically conductive linear body is projected (extended) outwardly from the hole at the tip of the sample holder. When a high voltage is applied to the electrically conductive linear body, the sample adhering to the tip of the electrically conductive linear body is ionized by electrospray. The ions are introduced to a mass spectrometer and are analyzed.

In accordance with the present invention, ionization can be performed under atmospheric pressure (in the atmosphere, in another inert gas or in a saturated vapor pressure chamber) without requiring that the sample holder or electrically conductive linear body be placed in a vacuum chamber. The sample can be used as is without being subjected to pretreatment. It is possible to use a biological sample as the sample, and electrospray can be produced even with regard to samples having a high salt concentration. Furthermore, the sample need not necessarily be diluted using a solvent (the invention naturally does not exclude dilution of the sample by a solvent). The diameter of the tip portion of the sample holder or of the electrically conductive linear body can be made small, thereby enabling application to extremely small amounts of sample, and it is also possible to improve the resolution of analysis. The electrically conductive linear body includes one obtained by coating with metal the surface of a needle made of an insulator such as glass (inclusive of quartz). If the diameter of the electrically conductive linear body can be made smaller in this way, a much higher resolution can be obtained.

The present invention further provides an ionization analyzing method of analyzing molecules that have been ionized by the ionization method described above.

By repeating the projecting and retracting of the electrically conductive linear body and the electrospraying of the sample multiple times with regard to a single sample and trapping ions within the analyzing apparatus or accumulating electric signals that are output from the analyzing apparatus, the S/N ratio can be improved.

By using an electrically conductive linear body at least the tip of which has been subjected to a hydrophobic or hydrophilic surface treatment, ion detection is possible in a time series in order of increasing surface activity with regard to all components having different surface activities within a liquid sample.

An ionization apparatus according to the present invention comprises: a support mechanism for supporting a hollow insulated sample holder having a small hole in a tip portion thereof; a driving unit for causing a tip portion of an electrically conductive linear body (inclusive of one that is needle-shaped), which has been inserted inside the sample holder, to project outwardly from or retract into the hole; and a high-voltage generating unit for applying a high voltage for electrospray to the linear body at least in a portion of a time period in which the tip of the linear body is being projected outwardly from the hole.

The present invention further provides an ionization analyzing apparatus having the above-mentioned ionization apparatus and an analyzing apparatus for analyzing ionized molecules.

DESCRIPTION OF THE PREFERRED EMBODIMENT

Figure 1:
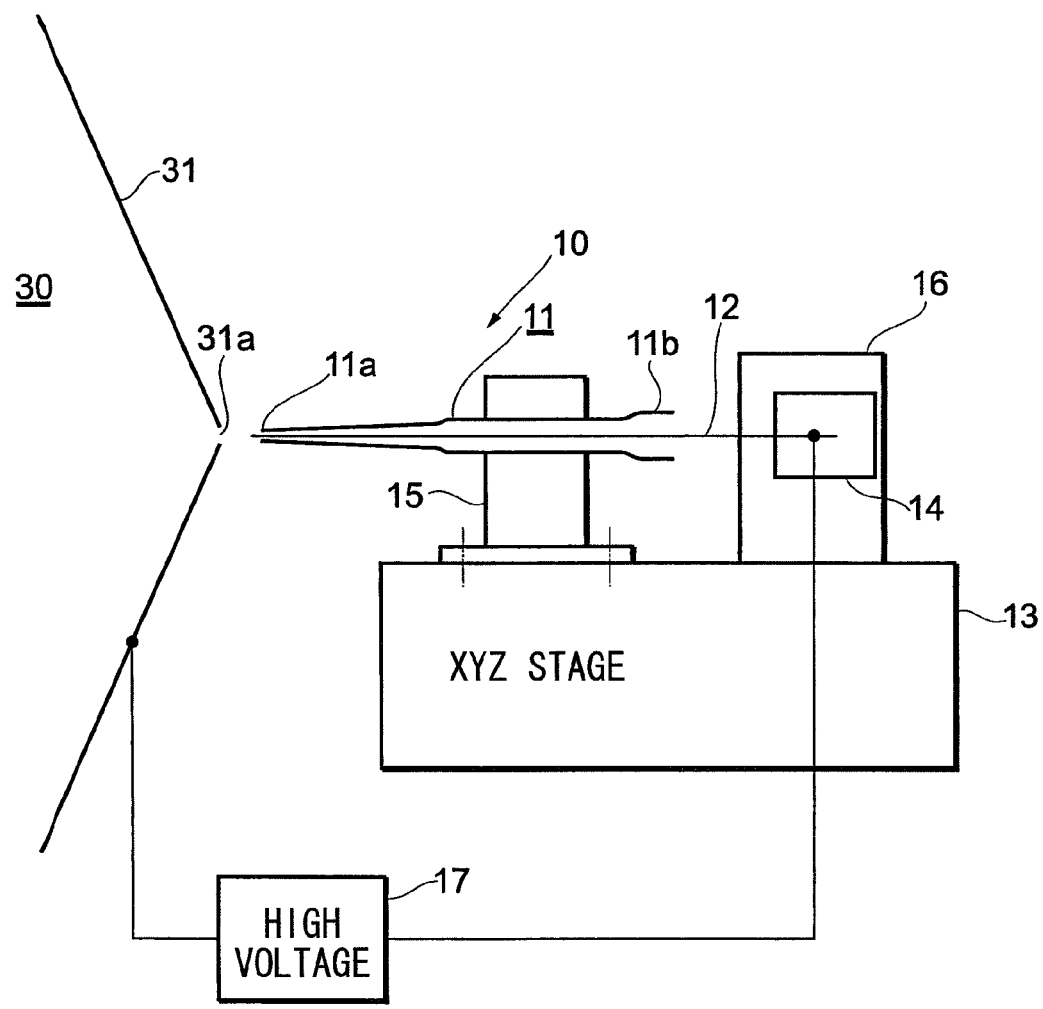
FIG. 1 illustrates the overall configuration of an ionization apparatus and ionization analyzing apparatus (analytical apparatus) according to an embodiment of the present invention.

FIG. 1 illustrates the general configuration of an ionization apparatus and ionization analyzing apparatus according to an embodiment of the present invention.

The ionization analyzing apparatus comprises an ionization apparatus 10 and a mass spectrometry apparatus (ion analyzing apparatus) 30.

Sample ions desorbed and ionized from a sample by the ionization apparatus 10 are introduced to the mass spectrometry apparatus 30. Although an (orthogonal) time-of-flight mass spectrometer can be mentioned as an example of the mass spectrometry apparatus, the present invention is also applicable to a mass spectrometry apparatus such as a (linear) ion-trapping mass spectrometry apparatus, a quadrupole mass spectrometry apparatus and a Fourier transform mass spectrometry apparatus. Further, an arrangement may be adopted in which an ion-trapping apparatus is placed as a preceding stage to a spectrometry apparatus, such as a time-of-flight mass spectrometry apparatus, with the exception of an ion-trapping mass spectrometry apparatus, ions that have been ionized in the ionization apparatus 10 are accumulated by the ion-trapping apparatus and the accumulated ions are subsequently introduced to the mass spectrometry apparatus (the details will be described later).

The interior of the mass spectrometry apparatus 30 is held in vacuum. The mass spectrometry apparatus 30 is equipped with a skimmer (orifice) 31 for ion sampling, the tip of the skimmer has an ion introduction hole (ion introduction path) 31a, and the interior of the mass spectrometry apparatus 30 is connected by the ion introduction hole 31a to the outside world (atmospheric pressure) in which the ionization apparatus 10 has been placed. There is also an analyzing apparatus having an ion sampling capillary rather than a skimmer as the ion introduction path. Depending upon the type of mass spectrometry apparatus, there is a type in which an ion focusing voltage (a comparatively low voltage of less than +100 V in case of a positive-ion mode and less than −100 V in case of a negative-ion mode) is applied to the ion sampling capillary (orifice) by a power supply unit. There are also cases where the ion sampling capillary is grounded. The outer wall of the mass spectrometry apparatus 30 generally is grounded.

The ionization apparatus 10 includes an XYZ stage 13; a support mechanism 15 provided on the XYZ stage 13 and supporting a hollow sample holder 11; a driving unit (actuator) 14 for driving a slender metal wire (an electrically conductive linear body) (inclusive of one having a tip tapered into the shape of a needle) 12 that has been inserted into the sample holder 11; and a high-voltage generating unit 17 for applying an electrospray high-voltage (on the order of several kV to 1 kV or less than 1 kV) across the slender metal wire 12 and the skimmer 31 of the mass spectrometry apparatus 30 (or ground or ground potential). The driving unit 14 is secured to the XYZ stage 13 by a support member 16.

In this embodiment, the electrically insulated sample holder 11 has the form of a glass capillary or pipette and has the shape of a slender cylinder overall, and comprises a central barrel portion having a uniform diameter; a tapered portion (tapered distal end, tip, tip-constituting portion) formed to have a tapered shape so as to be increasingly slender from the barrel portion to the tip 11a; and a base portion 11b connected to the barrel portion on the side opposite the tapered portion. The tip (tip portion) 11a of the sample holder 11 has an opening (small hole) of very small inner diameter. As one example, the inner diameter of the hole in the tip 11a may be 1 μm to several hundred μm depending upon the type and size of the sample, although the inner diameter may be less than 1 μm.

Figure 2:
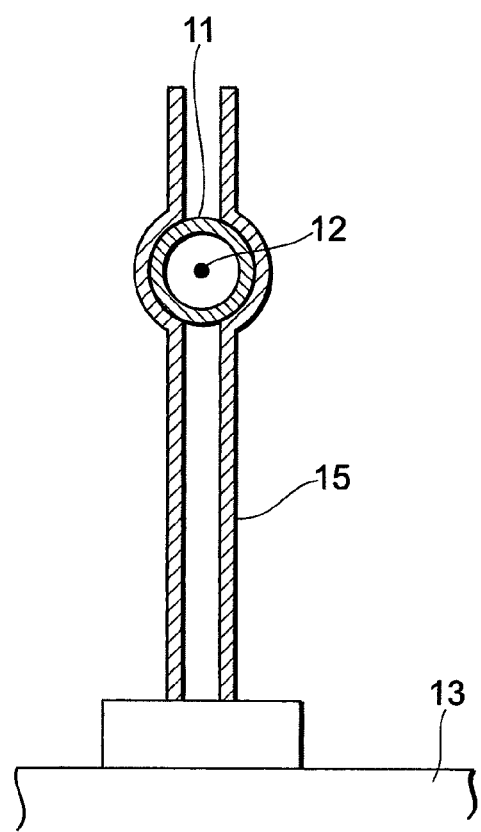
FIG. 2 is a sectional view illustrating an example of a sample holder supporting unit.

As shown in FIG. 2, the sample holder 11 is supported in a horizontal attitude by the support mechanism 15 composed of two clamp plates erected vertically on the XYZ stage 13 with a small clearance between them and formed to have arcuate recesses that clamp the barrel portion of the sample holder 11. The support mechanism 15 can be implemented in various forms, such as by being constituted by a support column erected on the XYZ stage 13 and an arm mounted on the upper portion of the support column and holding the sample holder 11, by way of example.

The slender metal wire 12 has been inserted into the sample holder 11 from the base portion 11b. It will suffice if the slender metal wire 12 has a diameter sized such that the wire will pass loosely through the hole (opening) in the tip 11a of sample holder 11, or if it has a diameter smaller than this. For example, the diameter of the slender metal wire 12 is ½ to 1/100 of the inner diameter of the hole in the tip 11a, or smaller. The tip of the slender metal wire 12 may or may not be tapered to a point. If necessary, a support member (e.g., a rubber stopper or the like having a center hole penetrated by the slender metal wire 12) (the support member preferably has an insulating property) supporting the slender metal wire 12 in a freely movable manner is placed inside the sample holder 11 (e.g., inside the barrel portion). The tip portion of the slender metal wire 12 may be in contact with the inner surface of the tip 11a (the inner side of the hole).

The driving unit 14 grasps the rear end portion of the slender metal wire 12 protruding outwardly from the base portion 11b of sample holder 11 and moves (displaces) (oscillates) (drives) the slender metal wire 12 along the longitudinal direction thereof. As a result of this driving operation, the tip portion of the slender metal wire 12 is projected (extended) outwardly from or retracted into the hole in the tip 11a of sample holder 11.

The XYZ stage 13 supports the support mechanism 15 of the sample holder 11 and the support member 16 of the driving unit 14 and displaces these as a whole in three orthogonal directions, namely along the X, Y, Z directions. For example, assume that the longitudinal direction of the slender metal wire 12 is the X direction. The position of the tip 11a of sample holder 11 is adjusted by the XYZ stage 13 so as to be situated in the proximity of, and external to along the X direction, the ion introduction hole 31a in the skimmer 31 of mass spectrometry apparatus 30. Naturally, an adjustment may be made such that when the tip of the slender metal wire 12 has been projected (extended) from the tip 11a of the sample holder 11, electrospray is generated without the tip of the slender metal wire 12 contacting the skimmer 31. The ionization of the sample is carried out under atmospheric pressure.

Preferably, the XYZ stage 13 and driving unit 14 include a device having a movement function exhibiting good mechanical reproducibility, such as a piezoelectric element or a motor-driven or magnetically driven device, and can control the amount of displacement on the nm order along each direction. In particular, it is preferred that the driving unit 14, which reciprocates the slender metal wire 12 in the longitudinal direction, be such that the frequency, amplitude and number of oscillations of reciprocation (in which an oscillation includes a single reciprocation) can be controlled.

Figure 3:
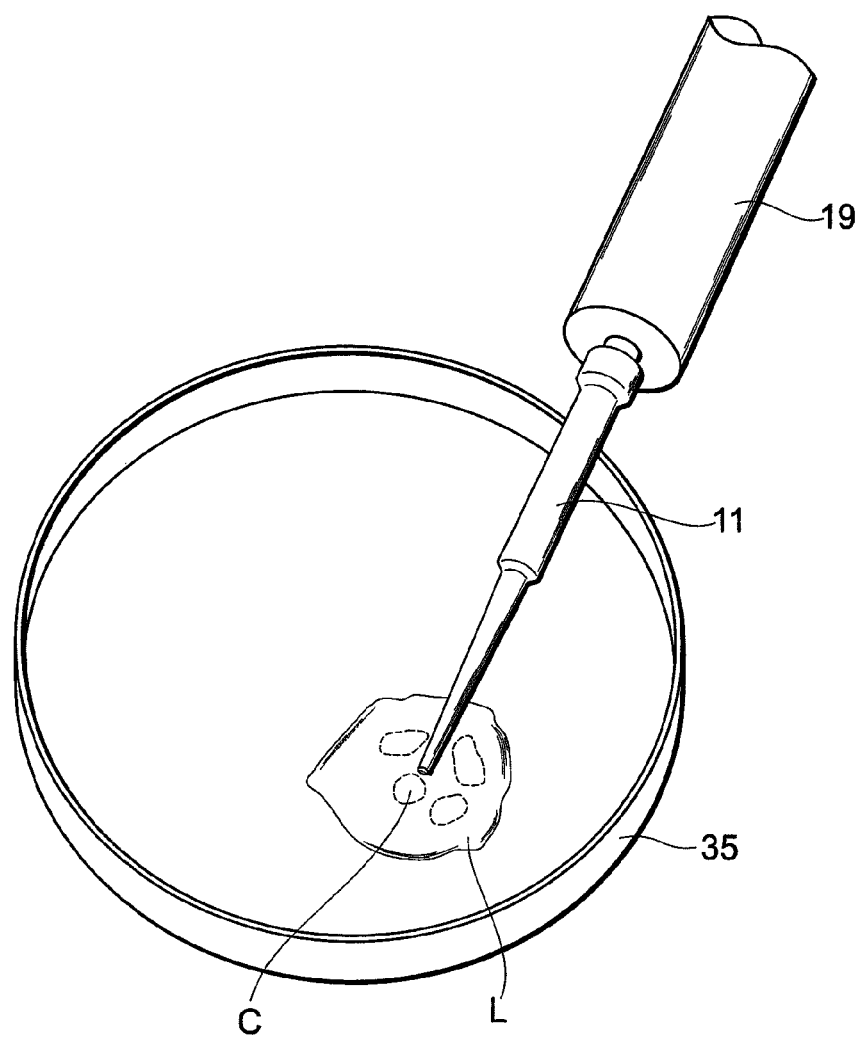
FIG. 3 is a perspective view illustrating the manner in which cell fluid within a cell is collected as a sample.

A sample of interest is taken in the following manner, by way of example: As shown in FIG. 3, a portion L of an organism has been placed inside a laboratory dish 35. The sample holder 11 is attached to a piston syringe 19. The contents (cell fluid) of a specific single cell C (the diameter of which is on the order of 10 to 100 μm) within the portion L of the organism are drawn inside the tip 11a (the interior of the tip or inside the tip portion) of sample holder 11 by the syringe 19. Only the cell fluid (the target sample) of the single cell C is taken as a sample inside the tip portion of the sample holder 11.

If cell fluid (e.g., less than 100 fL) that is less than 10% of the total cell fluid of the single cell can be sampled under a microscope, this will circumvent the need to sacrifice the living cell. In this case, after the cell fluid is drawn in, the interior of the sample holder (capillary) may be filled with a solvent (the solvent is drawn in) as necessary, thereby diluting the cell fluid sample (sampling of the sample multiple times need not be carried out). It is required that the tip of the sample holder be very slender, and it is required that the electrically conductive linear body inserted into the interior thereof also be made very slender. As will be described later, instead of a slender metal wire, an extremely slender electrically conductive linear body can be obtained as the electrically conductive linear body if the surface of a slender glass wire (of diameter 1 to 100 μm, for example) is coated with a metal (as by vapor-depositing the metal).

Figure 4:
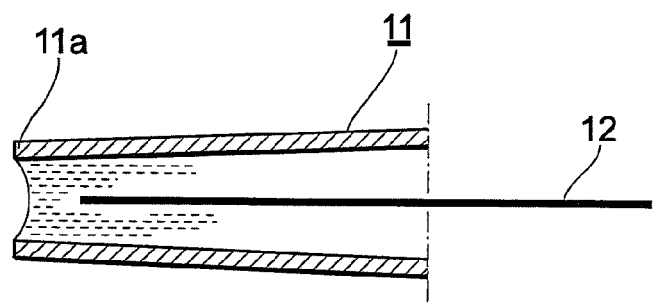
FIG. 4, which illustrates the tip portion of the sample holder in enlarged form, shows a slender metal wire in the retracted state.

The sample holder 11 that has sampled the contents of the cell C is attached and secured to the support mechanism 15, as shown in FIG. 1. The slender metal wire 12 is inserted from the base portion 11b of the sample holder 11. The tip of the slender metal wire 12 is situated on the inner side of the tip portion of sample holder 11 (see FIG. 4).

The sample of interest is not limited to a cell. The sample method also is not limited to that set forth above. In short, it will suffice if the sample to undergo mass spectrometry is introduced into the tip portion of the sample holder 11. The sample of interest may be a liquid or liquefied object. Owing to its surface tension, the liquid or liquefied object will not leak from the small hole in the tip 11a of sample holder 11. The tip (tip portion) of the slender metal wire 12 is situated inside the sample of interest (at the innermost position; top dead center or bottom dead center in accordance with the attitude of the sample holder).

Figure 5:
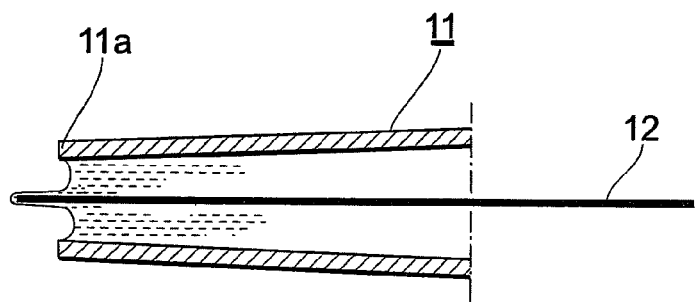
FIG. 5, which illustrates the tip portion of the sample holder in enlarged form, shows a slender metal wire in the projected (extended) state.

In this state the slender metal wire 12 is projected (extended) outwardly from the hole of the end 11a of the sample holder 11 (see FIG. 5). As the tip (tip portion) of the slender metal wire 12 is projected outwardly, the sample adheres to the tip (tip portion) of the slender metal wire 12 and is outwardly exposed. Owing to the surface tension of the liquefied sample, the adhesion of the sample to the tip (tip portion) of the slender metal wire 12 is suppressed to the minimum extent, the coating thereof is substantially uniformalized and the amount of sample also is made substantially constant (meaning that reproducibility is excellent).

The tip of the slender metal wire 12 moves through a predetermined amount of displacement between the inward position (innermost position or top dead center or bottom dead center) and outward position (outermost position or bottom dead center or top dead center) of the tip portion of sample holder 11. When the tip of the slender metal wire 12 arrives at the outermost position (e.g., a position several tens of microns to several millimeters distant from the tip 11a), a pulsed high voltage is applied across the slender metal wire 12 and skimmer 31. As a result, the sample adhered to the tip (tip portion) of the slender metal wire 12 is ionized by electrospray. The ionized sample is introduced to the interior of the mass spectrometry apparatus 30 from the introduction hole 31a of the skimmer 31 and undergoes mass spectrometry.

Preferably, the in-and-out movement (the projecting and retracting) of the slender metal wire 12 from the tip 11a of sample holder 11 and the application of the pulsed high voltage when the tip (tip portion) of the slender metal wire 12 is projected are repeated multiple times with regard to the same sample and ions are produced multiple times. In a case where the mass spectrometry apparatus is of the ion-trapping type, or if it is of the type having an ion-trapping apparatus provided as a preceding stage, the sample ions produced by the above-mentioned repetition will be accumulated by ion trapping and, hence, a mass spectrum having an excellent S/N ratio will be obtained. Further, a mass spectrum having an excellent S/N ratio can be obtained by electrically accumulating (as by storing data in memory) an electric signal output repeatedly from the mass spectrometry apparatus owing to the repetitive generation of ions.

When the liquid sample is consumed by electrospray from the tip of slender metal wire 12 and the metal surface of the slender wire becomes exposed, a gaseous discharge tends to occur. In such case, therefore, the voltage applied to the slender metal wire should be turned off before the discharge occurs. The pulse width of the voltage applied to the slender metal wire in such case usually is less than 1 ms.

The high voltage for electrospray may be applied to the slender metal wire 12 continuously. In this case the electrospray would be produced when the tip of the slender metal wire 12 protrudes outwardly from the sample.

The voltage applied to the slender metal wire 12 is a positive high potential in case of a positive-ion observation mode and is a negative high voltage in case of a negative-ion observation mode.

Figure 6:
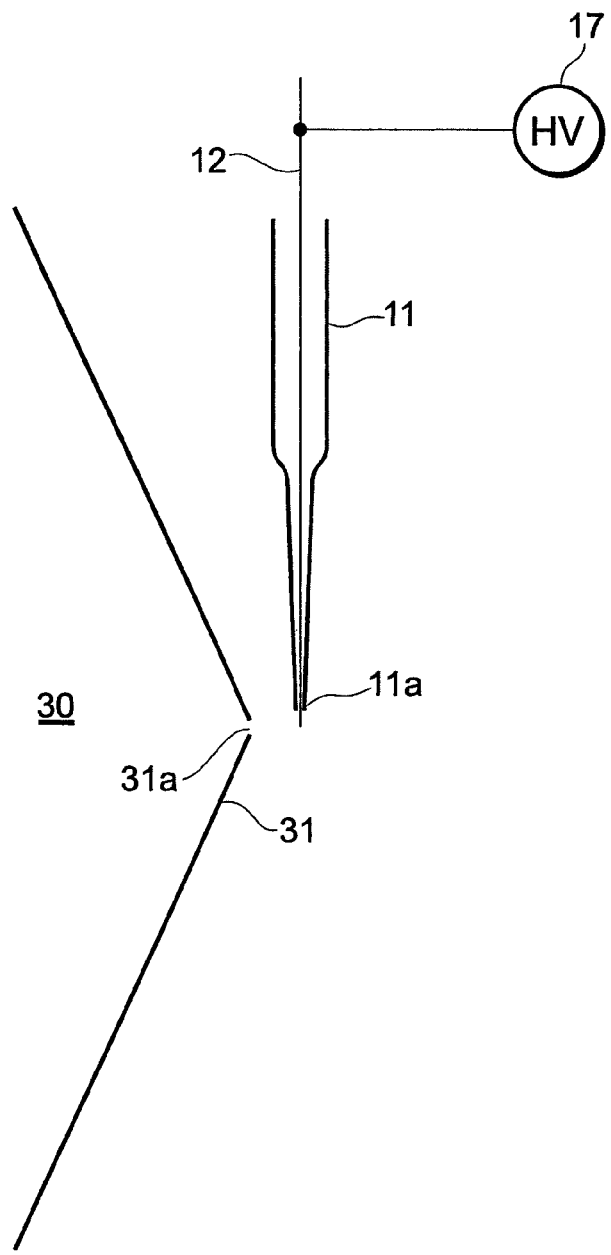
FIG. 6 illustrates another example of placement of a sample holder.

Although the sample holder 11 is arranged horizontally in FIG. 1, it may also be arranged vertically with the tip 11a pointed downward, as shown in FIG. 6. Conversely, the sample holder 11 may be arranged vertically with the tip 11a pointed upward. The sample holder 11 may be arranged at an incline. In any case, the sample holder 11 is placed at a position where the sample ions resulting from electrospray produced from the tip of the slender metal wire 12 will be introduced efficiently into the mass spectrometry apparatus 30 from the ion introduction hole 31a. It should be noted that the high-voltage generating unit 17 is illustrated in simplified form in FIG. 6 and in the diagrams that follow it.

Figure 7:
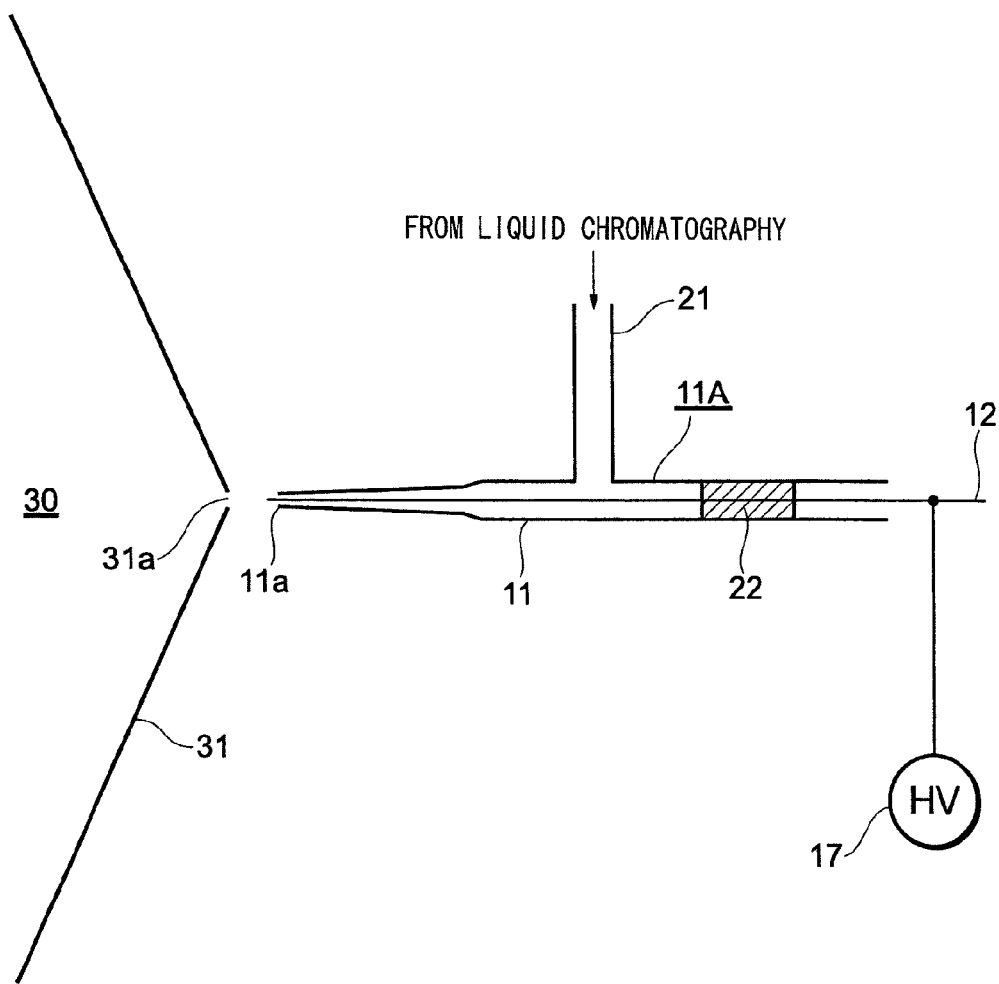
FIG. 7 illustrates another example of the configuration of a sample holder.

FIG. 7 illustrates a further embodiment. A sample holder 11A is configured in such a manner that a sample inflow passage 21 (a glass tube) is joined to the barrel portion of the above-mentioned sample holder 11 so as to communicate with therewith. Further, a sample-outflow preventing stopper 22 is used to plug the interior of the barrel portion on the base-end side of the portion to which the sample inflow passage 21 is connected. The sample-outflow preventing stopper 22 is made of, for example, rubber. The slender metal wire 12 penetrates the stopper 22 and extends up to the vicinity of the tip 11a (outwardly or inwardly thereof) of sample holder 11A.

By way of example, the sample inflow passage 21 can be connected to the outflow passage of liquid chromatography and the liquid outflow from liquid chromatography can be introduced into the sample holder 11A so that the liquid can undergo ionization and mass spectrometry.

Figure 8:
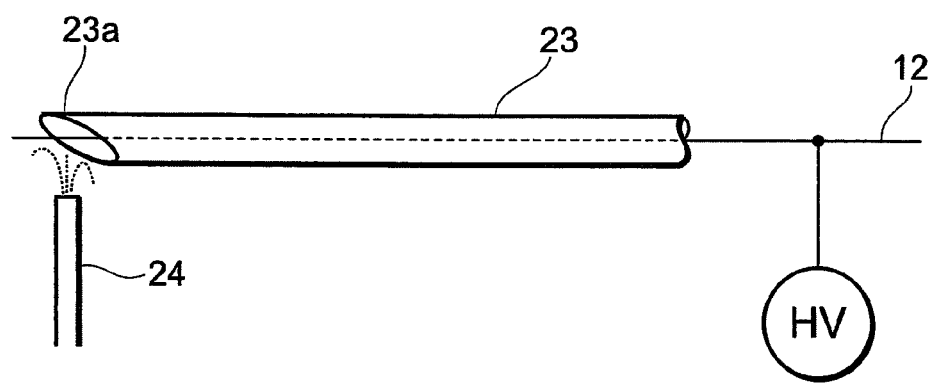
FIG. 8 illustrates another example of the configuration of a sample holder.

FIG. 8 illustrates a further embodiment, in which a capillary 23 made of glass is used as the sample holder and a tip portion 23a thereof is cut off at an angle. A plant or animal is pierced directly with the obliquely cut-off tip 23a of the capillary 23 to thereby take a sample. If necessary, it can be arranged so that a solvent vapor is blown (the solvent supplied) from a supply tube 24 toward the tip portion of the capillary 23 when the sample is ionized. The mass spectrometry apparatus is not shown in FIG. 8.

It should be noted that an arrangement may be adopted in which the driving unit 14 in FIG. 1 is omitted and the slender metal wire 12 is moved in and out (extended and retracted) via an insulator manually by the operator. Various modifications are conceivable. For example, the XYZ stage 13 is not necessarily required.

If the solvent is one that dissolves or moistens, any solvent may be used, and it may be in the form of a liquid or gas. Examples of the solvent are water, alcohol, acetic acid, trifluoroacetic acid, acetonitrile, an aqueous solution, a mixed solvent and a mixed gas, etc. These solvents can be supplied to the tip of the sample holder in the form of a liquid as is or upon being converted to a mist or heated vapor or in the form of a gas.

Figure 9:
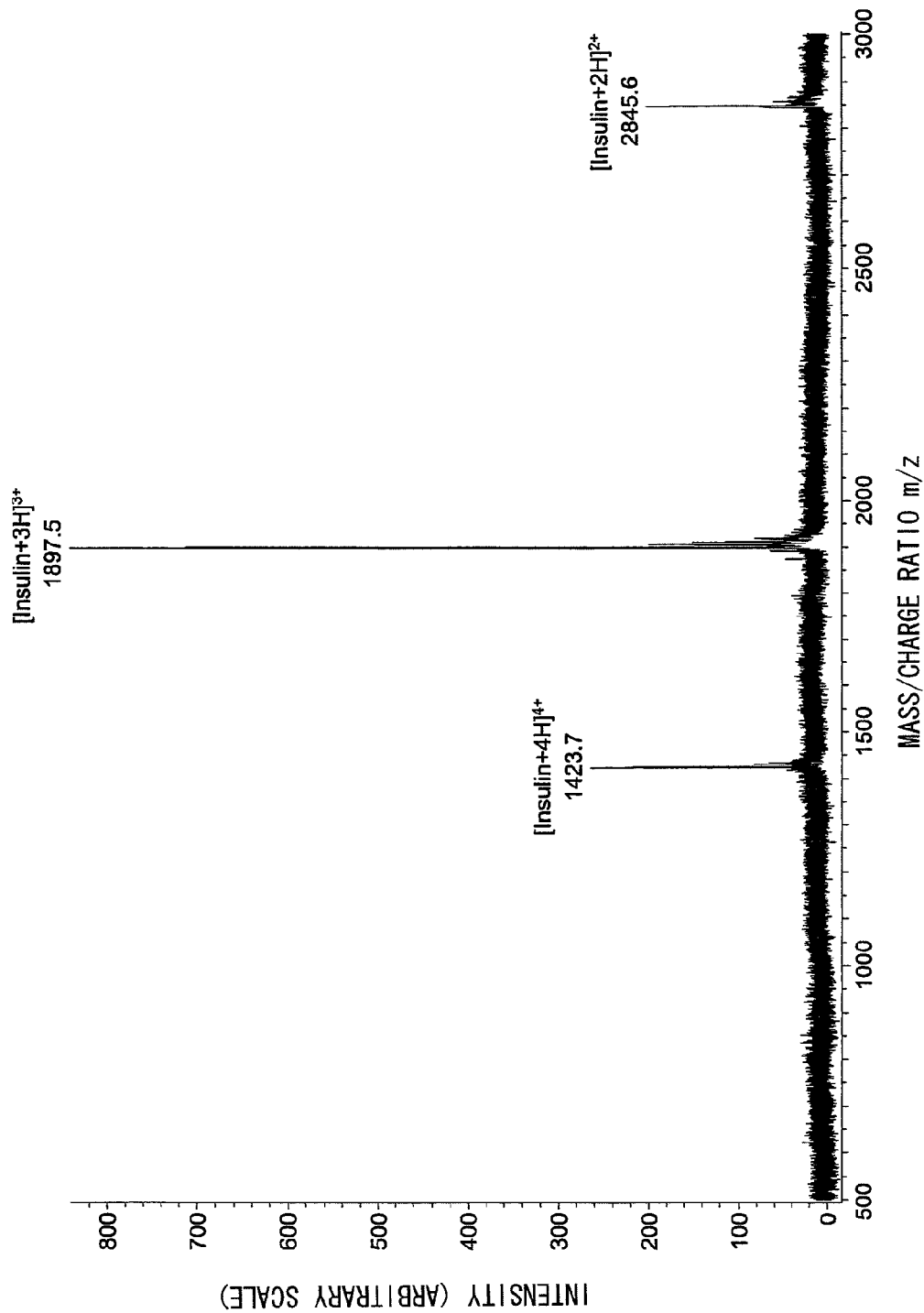
FIG. 9 is mass spectrum (graph) showing results of mass spectrometry based upon ionization with regard to an insulin solution.

Finally, ionization and result of analysis based thereon will be illustrated. FIG. 9 illustrates results obtained by using as the sample holder a capillary (the diameter of which is constant over the entire length) having an inner diameter of 250 µm, introducing an insulin solution, which has a volume of about 0.03 µL (microliters), onto the tip portion of the capillary, inserting a tungsten wire, which has a diameter of 10 µm, as the slender metal wire, moving the tip portion of the wire in and out of the capillary tip and applying a high voltage of 1.6 kV to thereby perform ionization and mass spectrometry by electrospray.

Figure 10:
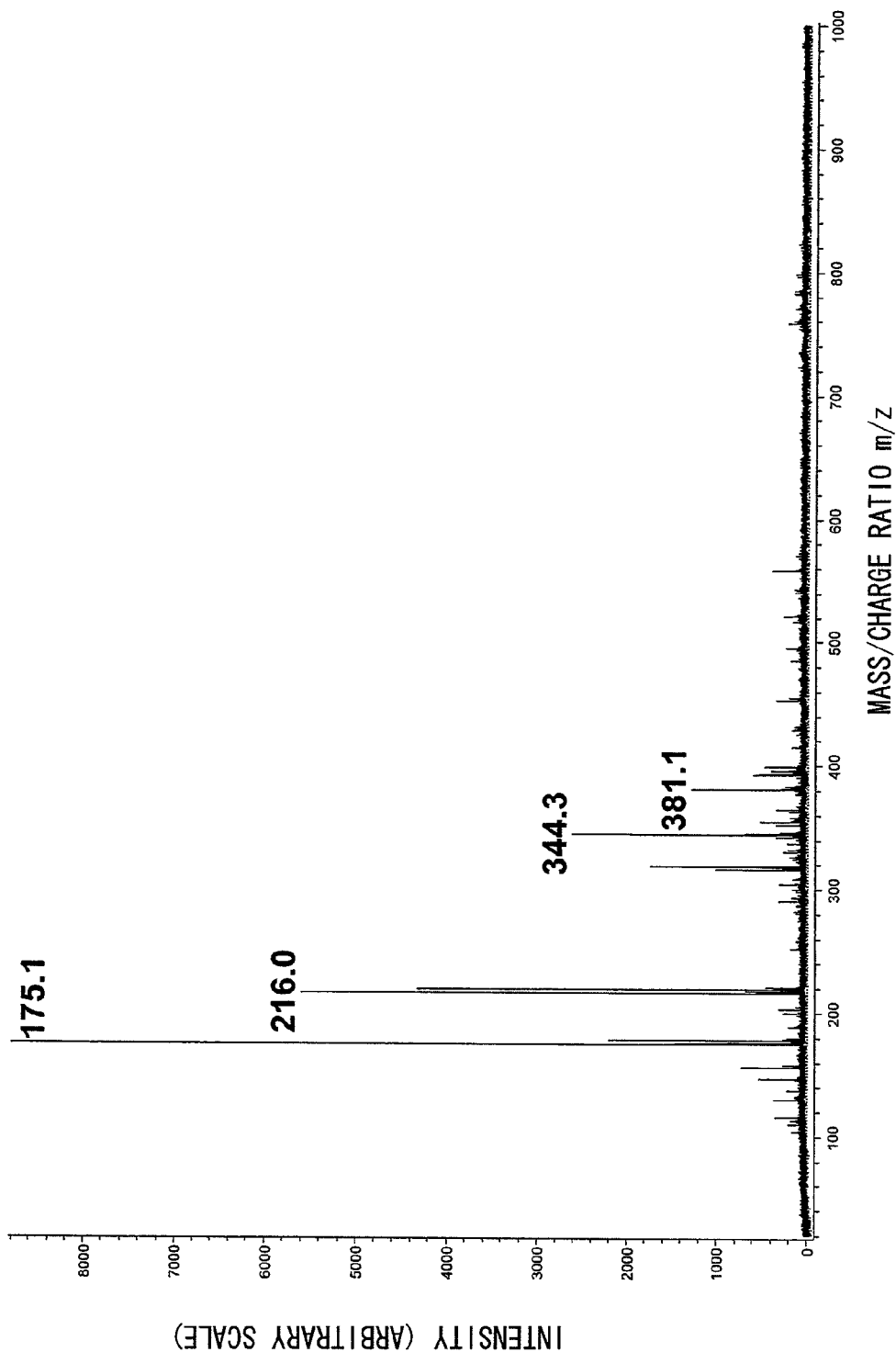
FIG. 10 is mass spectrum (graph) showing results of mass spectrometry based upon ionization with regard to a common onion.

FIG. 10 illustrates results obtained by piercing a common onion with a capillary (of inner diameter 250 µm) the tip of which has been cut off at an angle in the manner shown in FIG. 8, sampling the juice and inducing electrospray (at a voltage of 1.6 kV) by extending and retracting a tungsten wire having a diameter of 30 µm, thereby performing ionization and mass spectrometry. Water vapor was used as the solvent and this was sprayed toward the sample in the manner shown in FIG. 8. It will be understood that peaks appear for amino acids and sugars.

A body obtained by coating the surface (preferably the entire surface) of a linear body, which is made of an insulator such as glass (inclusive of quartz) and capable of being finely extended, with a metal (as by vapor-depositing the metal to a thickness of approximately 0.1 µm or less) can be used as the electrically conductive linear body. In accordance with this mode of implementation, it is possible to manufacture an electrically conductive linear body which is extremely slender (having a diameter of less than 10 µm).

In a case where a liquid sample has been introducing into the interior of the sample holder, an interface always exists between the solution and the atmosphere. Components in the solution that exhibit higher surface activity are concentrated at this interface. Accordingly, if these components can be electrosprayed selectively, then all of the components within the solution can be detected successively in order of surface activity. This becomes possible in accordance with the method of the present invention.

Specifically, the interior of a small sample holder (e.g., a capillary having an inner diameter on the millimeter order) is filled with a liquid sample. A slender probe that has undergone a (hydrophobic) surface treatment for rendering the surface hydrophobic is inserted inside the sample holder. The hydrophobic surface treatment can be performed as follows: For example, a titanium wire is exposed to a burner flame to thereby form an oxide film on the surface. This titanium probe is left standing in pentafluorophenyl-triethoxysilane (a 100% or 50% methanol solution) for from several hours to twenty-four hours. The surface of the titanium probe is made hydrophobic as a result. Making the surface of a slender probe hydrophilic also is efficacious.

A high voltage is applied to the probe beforehand. Alternatively, a high voltage is applied in pulsed fashion when the probe protrudes from the surface of the liquid sample.

The probe that has been inserted into the sample holder is moved back and forth (extended and retracted) (e.g., at 3 Hz) along the axis (longitudinal direction) of the sample holder, the probe is made to protrude forwardly from the liquid surface within the sample holder and the liquid sample that has adhered to the probe tip is electrosprayed slowly.

By virtue of this operation, first ions of high interface (surface) activity that have condensed selectively at the liquid interface (surface) are electrosprayed. By repeating this operation, ions are electrosprayed in order from ions of high to low surface activity. The spectra vary with time from components of high surface activity to components of low surface activity. Ions of all the analytes having different surface activities that are present in the liquid sample are thus detected.

With conventional electrospray, a liquid is fed through a capillary and a high voltage is applied to the capillary itself to thereby electrospray the liquid. In this case, all components contained in the liquid are forcibly fed simultaneously and are electrosprayed. Hence, components exhibiting little surface activity are not released from the charged droplets (they remain in the mother droplets during the offspring droplets formation). With regard to such components, therefore, detection as gaseous-phase ions is difficult and detection sensitivity is sacrificed. By contrast, in accordance with the present invention, a liquid sample is captured by a batch system within the sample holder and all droplets can be electrosprayed completely. That is, analysis of all components is possible. In particular, since a slender probe can be used (the tip diameter is less than one micrometer), the amount of sample captured is small and detailed fractionation can be performed in order of surface activity to thereby make component analysis possible.

When a probe surface is made hydrophilic, hydrophobic sample ions are observed. However, there are also cases where a hydrophilic sample will remain captured on the probe surface and will not be electrosprayed. In such cases ions will be observed if the probe tip is supplied with a solvent vapor to thereby promote electrospray. Accordingly, hydrophilic treatment is an excellent method of fractionating and electrospraying hydrophobic ions and hydrophilic ions.

What is claimed is:

1. An ionization method using electrospray comprising:
   introducing a sample into at least a tip portion of a hollow insulated sample holder having a small hole in the tip portion;
   supporting an electrically conductive linear body, which has been inserted inside said sample holder, such that a tip thereof is projectable outwardly from or retractable into said hole;
   projecting the tip of said linear body outwardly from the sample holder through said hole while being brought into contact with said sample inside said sample holder; and
   applying a high voltage for electrospray of several kV to 1 kV to said linear body after the tip of said electrically conductive linear body is projected outwardly from said hole of said sample holder, thereby ionizing, by electrospray, the sample adhering to the tip of said linear body, wherein the linear body is a solid wire.

2. An ionization method according to claim 1, wherein the projecting and retracting of the tip of said electrically conductive linear body and the electro spraying of the sample are repeated multiple times with regard to a single sample.

3. An ionization method according to claim 1, wherein application of said high voltage is halted when the sample at the tip of the electrically conductive linear body has been consumed by electrospray.

4. An ionization method according to claim 1, wherein a sample is taken directly at the tip of said sample holder.

5. An ionization method according to claim 1, wherein a liquid sample is supplied to said sample holder from liquid chromatography.

6. An ionization method according to claim 1, wherein ionization is carried out under atmospheric pressure.

7. An ionization method according to claim 1, further comprising using an electrically conductive linear body at least the tip of which has been subjected to a hydrophobic or hydrophilic surface treatment.

8. An ionization analyzing method of analyzing molecules that have been ionized by the ionization method set forth in claim 1.

9. An ionization method according to claim 2, wherein a sample is taken directly at the tip of said sample holder.

10. An ionization method according to claim 3, wherein a sample is taken directly at the tip of said sample holder.

11. An ionization method according to claim 2, wherein a liquid sample is supplied to said sample holder from liquid chromatography.

12. An ionization method according to claim 3, wherein a liquid sample is supplied to said sample holder from liquid chromatography.

13. An ionization method according to claim 2, wherein ionization is carried out under atmospheric pressure.

14. An ionization method according to claim 3, wherein ionization is carried out under atmospheric pressure.

15. An ionization method according to claim 2, further comprising using an electrically conductive linear body at least the tip of which has been subjected to a hydrophobic or hydrophilic surface treatment.

16. An ionization method according to claim 3, further comprising using an electrically conductive linear body at least the tip of which has been subjected to a hydrophobic or hydrophilic surface treatment.

17. An ionization method according to claim 6, further comprising using an electrically conductive linear body at least the tip of which has been subjected to a hydrophobic or hydrophilic surface treatment.

18. An ionization analyzing method of analyzing molecules that have been ionized by the ionization method set forth in claim 2.

* * * * *